United States Patent [19]

Vogtel et al.

[11] Patent Number: 5,264,624
[45] Date of Patent: Nov. 23, 1993

[54] PROCESS FOR THE RECOVERY OF ADIPIC ACID

[75] Inventors: Peter Vogtel, Leverkusen; Georg Steinhoff, Krefeld, both of Fed. Rep. of Germany

[73] Assignee: Bayer Aktiengesellschaft, Leverkusen, Fed. Rep. of Germany

[21] Appl. No.: 841,958

[22] Filed: Feb. 26, 1992

[30] Foreign Application Priority Data

Mar. 5, 1991 [DE] Fed. Rep. of Germany ....... 4106937

[51] Int. Cl.$^5$ .............................................. C07C 51/42
[52] U.S. Cl. ..................................................... 562/513
[58] Field of Search .......................................... 562/513

[56] References Cited

U.S. PATENT DOCUMENTS

| 2,713,067 | 7/1955 | Hamblet et al. | 260/537 |
| 3,096,369 | 7/1963 | Soeterbroek et al. | 260/537 |
| 3,476,805 | 11/1969 | Vollinger et al. | 260/531 |
| 3,818,081 | 6/1974 | Adamek | 260/537 P |
| 4,014,903 | 3/1977 | Moore | 260/345.9 |
| 4,254,283 | 3/1981 | Mock | 562/513 |

FOREIGN PATENT DOCUMENTS 54-115314  6/1979  Japan.
745063    2/1956  United Kingdom.

*Primary Examiner*—José G. Dees
*Assistant Examiner*—Joseph M. Conrad, III
*Attorney, Agent, or Firm*—Joseph C. Gil; Richard E. L. Henderson

[57] ABSTRACT

This invention relates to a process for the recovery of adipic acid from mother liquors collected during commercial production of adipic acid, wherein said mother liquors contain from 52 to 60% by weight of nitric acid calculated as $HNO_3$, not taking into account the organic constituents, from 2 to 6% by weight of succinic acid, from 4 to 9% by weight of glutaric acid, and from 5 to 10% by weight of adipic acid, by selective crystallization of the adipic acid dissolved in said mother liquors by (a) adding an aqueous adipic acid solution having an adipic acid content of from 0.5 to 6% by weight to said mother liquor in the temperature range of from 30° to 60° C. in such a quantity that the concentration of nitric acid in the mixture is reduced to 35 to 50% by weight;

(b) cooling the mixture by at least 5 degrees Celsius within a period of from 0.5 to 5 hours to induce crystallization of the adipic acid;

(c) isolating the crystallized adipic acid by filtration; and (d) transferring the filtrate obtained in step (c) to a distillation apparatus for distillative workup of the glutaric acid contained therein.

2 Claims, No Drawings

PROCESS FOR THE RECOVERY OF ADIPIC ACID

BACKGROUND OF THE INVENTION

This invention relates to a new process for the recovery of adipic acid from the separated stream of by-products obtained from the oxidation of commercial mixtures of cyclohexanol/cyclohexanone with nitric acid and isolation of most of the resultant adipic acid by crystallization. At the same time, the distillation residue obtained after distillative workup of the glutaric acid left in the mother liquor from the process is put to a useful purpose.

Glutaric and succinic acid are obtained as by-products in the preparation of adipic acid by oxidation of commercial mixtures of cyclohexanol and cyclohexanone using nitric acid. Compared with adipic acid, glutaric and succinic acid are concentrated to the greatest extent in the mother liquor from the adipic acid crystallization. Part of this mother liquor is therefore discharged from the process to prevent the accumulation of by-products. After the separation of nitric acid and water, the dicarboxylic acid mixture obtained may be worked up by distillation to yield "technical glutaric acid". The distillation residue thus obtained contains mainly adipic acid, coking products, and metal catalysts such as copper or vanadium.

The adipic acid present in the dicarboxylic acid mixture (about 25 to 35% by weight) is lost as adipic acid. This adipic acid impairs the quality of the technical glutaric acid obtained, thereby impairing the usefulness of technical glutaric acid for tanning, and increases the quantity of residue from the distillative workup of glutaric acid.

Numerous processes have therefore been developed for the recovery of adipic acid. According to U.S. Pat. No. 3,790,626, adipic acid may be extracted, for example, with cyclohexanol and/or cyclohexanone. According to U.S. Pat. No. 4,146,730, glutaric and succinic acid form adducts with urea, from which adipic acid can be separated.

The conversion of glutaric and succinic acids into imides and their separation has also been described. U.S. Pat. No. 3,818,081). The reaction with alkylamine converts glutaric and succinic acid into amides, which are then separated from adipic acid (European Patent Application 33,851). U.S. Pat. No. 4,442,303 describes the esterification of dicarboxylic acids and the workup and separation of the resultant esters.

Various crystallization processes have also been described in the literature. U.S. Pat. No. 4,014,903 describes a simple cooling crystallization for the recovery of adipic acid from the separated stream of by-products. Experiments have shown, however, that the efficiency of such a process is unsatisfactory for carrying out on a technical scale because the quantity which crystallizes is too small, a large quantity of succinic acid crystallizes at the same time, heavy deposits cake to the walls of the vessels and cooling coils, and the speed of crystallization is too low because the solution frequently remains supersaturated even after about three hours.

According to U.S. Pat. No. 4,254,283, the crystallization of succinic acid that occurs at the same time is accepted and the resulting mixture of adipic acid and succinic acid is separated by distillation. The addition of sulfuric acid and water to the dicarboxylic acid mixture and the recovery of adipic acid by crystallization has also been described. "Separating and Recovering Adipic Acid", Japanese Kokai 54-115314.

It has now surprisingly been found that the disadvantages of cooled crystallization for the recovery of adipic acid can be avoided if the $HNO_3$ concentration is reduced from about 52–60% by weight (preferably 55–60% by weight) to about 35–50% by weight (preferably to about 45% by weight) before the onset of crystallization by the addition of an aqueous adipic acid solution having an adipic acid content of from about 0.5 to about 6% by weight (preferably a saturated solution) and the adipic acid concentration is at the same time kept constant or even increased. When calculating these concentrations the above-mentioned percentage concentrations of $HNO_3$ for the purposes of this invention, always refer to the quantity of nitric acid and water present in the solution without taking into account the organic constituents. Due to the operation of the process according to the invention, more adipic acid crystallizes because of its low solubility in dilute $HNO_3$. The portion of adipic acid introduced with the added aqueous solution is thereby overcompensated for several times over. Crystallization proceeds more rapidly due to the higher relative super-saturation and the presence of crystallization nuclei in the added adipic acid solution. The precipitate can easily be filtered. Significantly less succinic acid crystallizes at the same time because the succinic acid concentration, in contrast to the adipic acid concentration, is lowered and because less succinic acid is precipitated due to the more rapid crystallization of adipic acid. The same applies to the reduction in the amount of deposit caked to the cooling surfaces. Both these factors enable crystallization to take place at lower temperatures and hence to increase the degree of adipic acid separation.

SUMMARY OF THE INVENTION

This invention thus relates to a process for the recovery of adipic acid from mother liquors collected in an initial crystallization step during commercial production of adipic acid by oxidation of mixtures of cyclohexanol and cyclohexanone using nitric acid, wherein said mother liquors contain from about 52 to about 60% by weight of nitric acid calculated as $HNO_3$, not taking into account the organic constituents, from about 2 to about 6% by weight of succinic acid, from about 4 to about 9% by weight of glutaric acid, and from about 5 to about 10% by weight of adipic acid, by selective crystallization of the adipic acid dissolved in said mother liquors comprising (a) adding an aqueous adipic acid solution having an adipic acid content of from about 0.5 to about 6% by weight to said mother liquor in the temperature range of from about 30° to about 60° C. in such a quantity that the concentration of nitric acid in the mixture is reduced to about 35 to about 50% by weight;

(b) cooling the mixture by at least 5 degrees Celsius within a period of from about 0.5 to about 5 hours to induce crystallization of the adipic acid;

(c) isolating the crystallized adipic acid by filtration; and (d) transferring the filtrate obtained in step (c) to a distillation apparatus for distillative workup of the glutaric acid contained therein.

DETAILED DESCRIPTION OF THE INVENTION

As already mentioned above, the commercial production of adipic acid is carried out by the oxidation of commercial mixtures of cyclohexanol and cyclohexanone by means of nitric acid. The main quantity of adipic acid formed is isolated from the resulting reaction mixture by crystallization. The mother liquor thus obtained contains most of the succinic acid and glutaric acid formed as by-products in addition to further quantities of adipic acid. The portion of mother liquor removed from the process to prevent the accumulation of these by-products constitutes the starting material for the process according to the invention. This aqueous solution is characterized by containing nitric acid, succinic acid, glutaric acid, and adipic acid at the concentrations mentioned above. To carry out the process according to the invention, this starting solution is mixed with an aqueous solution of adipic acid having an adipic acid content of from about 0.5 to about 6% by weight (preferably a saturated aqueous adipic acid solution) at a temperature in the range of from 30° to 60° C., the quantity of aqueous adipic acid solution added being calculated to lower the nitric acid content of the resulting mixture to about 35 to 50% by weight (preferably to about 45% by weight). The mixture thus obtained is then cooled by at least 5 degrees Celsius (preferably to 20° C.) over a period of from about 0.5 to about 5 hours (preferably 1.5 hours). The adipic acid that then crystallizes with a degree of purity of at least 90% by weight is isolated by filtration and the remaining solution is transferred to a distillation apparatus for the workup of glutaric acid.

The distillation residue obtained from the distillative workup of glutaric acid contains about 70 to 80% by weight of adipic acid and may be used for the preparation of the aqueous solution that is added to the starting solution in the process according to the invention.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

Example 1 (Blank Test)

No significant quantity of adipic acid crystallizes from the supersaturated solution of Example 1 even after 3 hours.

Example 2 (Comparison Test)

The quantity of mother liquor used in Example 2 is cooled by 7 degrees Celsius within 3 hours without the addition of an aqueous adipic acid solution, which is an essential requirement of this invention. The cooled solution remains supersaturated with adipic acid and the small quantity of adipic acid which does crystallize is contaminated with about 10% of succinic acid.

Example 3 (According To The Invention)

Example 3 shows that a lowering of the nitric acid concentration results in a marked increase in the quantity of crystallizing adipic acid, even without cooling.

Examples 4 And 5 (According To The Invention)

Examples 4 and 5 show that a considerable quantity of adipic acid present in solution in the mother liquor can be crystallized by the process according to the invention without a sharp increase in the quantity of succinic acid precipitating at the same time.

Experimental parameters and results for Examples 1 to 5 are summarized in the following Tables 1 and 2.

TABLE 1

| | Experimental Parameters | | | | | | | | | |
|---|---|---|---|---|---|---|---|---|---|---|
| | Quantity of mother liquor | | Dilution | | Composition of Solution | | | Start temp. | End temp. | Cooling time |
| Example | abs [kg] | a.a. diss. [kg] | abs [kg] | a.a. diss. [kg] | % HNO$_3$ org. free | % a.a. in soln. | Σ a.a. [kg] | [°C.] | [°C.] | [°C.] |
| 1 | 4000 | 228.5 | — | — | 55.3 | 5.7 | 228.5 | 32 | 31 | 3 |
| 2 | 4000 | 228.5 | — | — | 55.3 | 5.7 | 228.5 | 32 | 25 | 3 |
| 3 | 4000 | 228.5 | 515 | 15.6 | 48.2 | 5.4 | 244.1 | 32 | 31 | 3 |
| 4 | 4000 | 228.5 | 515 | 15.6 | 48.2 | 5.4 | 244.1 | 32 | 25 | 3 |
| 5 | 4000 | 228.5 | 515 | 15.6 | 48.2 | 5.4 | 244.1 | 32 | 20 | 3 |

Abbreviations:
a.a. = adipic acid
s.a. = succinic acid
g.a. = glutaric acid
a.a. diss. = dissolved adipic acid
% HNO$_3$ org. free = concentration of nitric acid based on HNO$_3$ and water without including the organic constituents
Σ a.a. = total quantity of a.a.
a.a. recov. = recovered adipic acid equal to the difference between the total quantity of adipic acid and the quantity of adipic acid added in the form of the diluting solution

TABLE 2

| | Results | | | | | | | | |
|---|---|---|---|---|---|---|---|---|---|
| | Filtrate | | | Crystals | | | | | a.a. recoverd |
| | Quantity | % a.a. | a.a. abs | Quantity | Composition | | | a.a. | |
| Example | [kg] | in soln. | [kg] | [kg] | % s.a. | % g.a. | % a.a. | [kg] | [kg] |
| 1 | 3990 | 5.4 | 218.5 | 10 | 0 | 0 | 100 | 10 | 10 |
| 2 | 3907 | 3.8 | 149.4 | 89.6 | 9.3 | 0.5 | 90.2 | 80 | 80 |
| 3 | 4398 | 3.1 | 138.4 | 107.6 | 1.3 | 0.9 | 97.9 | 105.5 | 90 |
| 4 | 4368 | 2.1 | 91.7 | 157.0 | 2.2 | 0.9 | 96.8 | 152.3 | 136.7 |

TABLE 2-continued

| Example | Filtrate Quantity [kg] | Filtrate % a.a. in soln. | a.a. abs [kg] | Crystals Quantity [kg] | Crystals Composition % s.a. | Crystals Composition % g.a. | % a.a. | a.a. [kg] | a.a. recoverd [kg] |
|---|---|---|---|---|---|---|---|---|---|
| 5 | 4342 | 1.8 | 78.5 | 174.7 | 4.2 | 0.9 | 94.9 | 166.1 | 150.5 |

For Abbreviations see Table 1.

What is claimed is:

1. A process for the recovery of adipic acid from mother liquors collected in an initial crystallization step during commercial production of adipic acid by oxidation of mixtures of cyclohexanol and cyclohexanone using nitric acid, wherein said mother liquors contain from 52 to 60% by weight of nitric acid calculated as $HNO_3$, not taking into account the organic constituents, from 2 to 6% by weight of succinic acid, from 4 to 9% by weight of glutaric acid, and from 5 to 10% by weight of adipic acid, by selective crystallization of the adipic acid dissolved in said mother liquors comprising (a) adding an aqueous adipic acid solution having an adipic acid content of from 0.5 to 6% by weight to said mother liquor in the temperature range of from 30° to 60° C. in such a quantity that the concentration of nitric acid in the mixture is reduced to 35 to 50% by weight;

(b) cooling the mixture by at least 5 degrees Celsius within a period of from 0.5 to 5 hours to induce crystallization of the adipic acid;

(c) isolating the crystallized adipic acid by filtration; and (d) transferring the filtrate obtained in step (c) to a distillation apparatus for distillative workup of the glutaric acid contained therein.

2. A process according to claim 1 wherein the distillation residue obtained from the distillative working up of glutaric acid in step (d) and consisting substantially of adipic acid is used for the preparation of the aqueous adipic acid solution (a).

* * * * *